(12) United States Patent
Garrett et al.

(10) Patent No.: US 11,100,492 B2
(45) Date of Patent: Aug. 24, 2021

(54) GENERAL PURPOSE RE-LOADABLE CARD AGGREGATION IMPLEMENTATION

(71) Applicants: Peter Garrett, Aromas, CA (US); Paz Rheinstein, Aromas, CA (US); Mark Boys, Aromas, CA (US)

(72) Inventors: Peter Garrett, Aromas, CA (US); Paz Rheinstein, Aromas, CA (US); Mark Boys, Aromas, CA (US)

( * ) Notice: Subject to any disclaimer, the term of this patent is extended or adjusted under 35 U.S.C. 154(b) by 0 days.

(21) Appl. No.: 16/252,685

(22) Filed: Jan. 20, 2019

(65) Prior Publication Data
US 2020/0286074 A1    Sep. 10, 2020

Related U.S. Application Data (60) Provisional application No. 62/631,945, filed on Feb. 19, 2018.

(51) Int. Cl.
G06Q 20/34        (2012.01)
G06K 19/07       (2006.01)

(52) U.S. Cl.
CPC ....... *G06Q 20/349* (2013.01); *G06K 19/0723* (2013.01); *G06Q 20/341* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,590,038 A * | 12/1996 | Pitroda | .................. | G06Q 50/22 705/41 |
| 6,889,899 B2 * | 5/2005 | Silberberg | ............. | G07B 15/02 235/384 |
| 7,280,847 B2 * | 10/2007 | Goldthwaite | ........ | G06K 7/0004 370/310 |
| 7,784,692 B1 * | 8/2010 | Arrington, III | ...... | G06K 7/0008 235/451 |
| 7,949,373 B2 * | 5/2011 | Whiting | ........... | G06K 19/06187 455/557 |
| 8,083,141 B1 * | 12/2011 | Courtright | ............ | G07F 7/0846 235/383 |
| 8,498,936 B2 * | 7/2013 | Cai | ....................... | G06Q 20/105 705/41 |
| 8,538,845 B2 * | 9/2013 | Liberty | .............. | G06Q 20/0855 705/35 |
| 8,600,863 B2 * | 12/2013 | Jain | ........................ | G07F 7/0846 705/37 |
| 8,671,055 B2 * | 3/2014 | Spodak | .............. | G06Q 20/3552 705/41 |
| 8,825,532 B1 * | 9/2014 | Wong | ..................... | G06Q 20/16 705/21 |
| 8,827,164 B2 * | 9/2014 | Jolivet | ............... | G06Q 20/3227 235/492 |
| 9,691,059 B1 * | 6/2017 | Courtright | ......... | G06Q 20/3223 |

(Continued)

*Primary Examiner* — Daniel I Walsh (57) ABSTRACT

A method and apparatus is taught wherein a light smartcard may be utilized to make transactions so that a user only has to carry one card and not be encumbered with the multiple cards that now have to deal with. This is accomplished with a third party API service provider. This could also be thought of as your own personal cloud that carries only your cards and only your information including virtual currencies as well. Now you only have to carry one and one card only. You can spend from any of your other accounts through this one card.

10 Claims, 5 Drawing Sheets

(56) References Cited

U.S. PATENT DOCUMENTS

| | | | | |
|---|---|---|---|---|
| 10,026,078 B1* | 7/2018 | Nolan | | G06Q 20/3572 |
| 10,614,450 B1* | 4/2020 | Templeton | | G06Q 20/105 |
| 10,755,533 B2* | 8/2020 | Rodriguez Bravo | | G06K 19/07 |
| 10,810,570 B1* | 10/2020 | Martin | | G06K 7/10297 |
| 2002/0114130 A1* | 8/2002 | Schremmer | | H04B 1/3816 |
| | | | | 361/679.56 |
| 2002/0134837 A1* | 9/2002 | Kishon | | G06K 7/084 |
| | | | | 235/449 |
| 2003/0085288 A1* | 5/2003 | Luu | | H04W 88/02 |
| | | | | 235/492 |
| 2003/0155423 A1* | 8/2003 | Limelette | | G06K 19/07726 |
| | | | | 235/492 |
| 2003/0213849 A1* | 11/2003 | Luu | | G06K 19/07739 |
| | | | | 235/492 |
| 2003/0222152 A1* | 12/2003 | Boley, Jr. | | G06K 19/06187 |
| | | | | 235/492 |
| 2004/0087339 A1* | 5/2004 | Goldthwaite | | G06Q 20/341 |
| | | | | 455/558 |
| 2004/0124246 A1* | 7/2004 | Allen | | G07F 7/1008 |
| | | | | 235/492 |
| 2004/0171406 A1* | 9/2004 | Purk | | G06K 19/07703 |
| | | | | 455/558 |
| 2005/0269402 A1* | 12/2005 | Spitzer | | G07F 7/0886 |
| | | | | 235/380 |
| 2006/0091223 A1* | 5/2006 | Zellner | | G06Q 20/10 |
| | | | | 235/492 |
| 2006/0287004 A1* | 12/2006 | Fuqua | | G06Q 20/0658 |
| | | | | 455/558 |
| 2007/0055630 A1* | 3/2007 | Gauthier | | G06Q 20/24 |
| | | | | 705/44 |
| 2007/0114274 A1* | 5/2007 | Gibbs | | G06Q 20/385 |
| | | | | 235/380 |
| 2007/0131759 A1* | 6/2007 | Cox | | G06K 19/0718 |
| | | | | 235/380 |
| 2007/0185820 A1* | 8/2007 | Talker | | G06Q 20/3674 |
| | | | | 705/67 |
| 2007/0262139 A1* | 11/2007 | Fiebiger | | G06Q 20/40 |
| | | | | 235/380 |
| 2011/0047074 A1* | 2/2011 | Cai | | G07F 7/0886 |
| | | | | 705/41 |
| 2011/0140841 A1* | 6/2011 | Bona | | G07F 7/0846 |
| | | | | 340/5.83 |
| 2012/0123935 A1* | 5/2012 | Brudnicki | | G06Q 20/405 |
| | | | | 705/41 |
| 2013/0185201 A1* | 7/2013 | Jain | | G06K 19/0711 |
| | | | | 705/41 |
| 2013/0211935 A1* | 8/2013 | Brenny | | G06Q 20/349 |
| | | | | 705/17 |
| 2014/0001263 A1* | 1/2014 | Babu | | G06Q 20/3278 |
| | | | | 235/440 |
| 2014/0006277 A1* | 1/2014 | Rao | | G06Q 20/3572 |
| | | | | 705/41 |
| 2014/0138449 A1* | 5/2014 | Goldman | | G06K 19/06206 |
| | | | | 235/492 |
| 2014/0279476 A1* | 9/2014 | Hua | | G06Q 20/341 |
| | | | | 705/41 |
| 2015/0069126 A1* | 3/2015 | Leon | | G06K 19/06206 |
| | | | | 235/449 |
| 2015/0134513 A1* | 5/2015 | Olson | | G06K 19/06206 |
| | | | | 705/39 |
| 2015/0248664 A1* | 9/2015 | Makhdumi | | G06Q 20/3276 |
| | | | | 235/380 |
| 2015/0348018 A1* | 12/2015 | Campos | | G06Q 20/12 |
| | | | | 705/41 |
| 2017/0213120 A1* | 7/2017 | Bae | | G06F 3/0488 |
| 2018/0189527 A1* | 7/2018 | Kim | | G06K 7/10316 |
| 2019/0019195 A1* | 1/2019 | Dunjic | | G06Q 20/4016 |
| 2019/0391720 A1* | 12/2019 | Choi | | G06Q 20/3278 |
| 2020/0005269 A1* | 1/2020 | Ou | | G06Q 20/3555 |
| 2020/0286074 A1* | 9/2020 | Garrett | | G06Q 20/341 |

\* cited by examiner

GENERAL PURPOSE RE-LOADABLE CARD AGGREGATION IMPLEMENTATION

CROSS-REFERENCE TO RELATED DOCUMENTS

This application claims priority to U.S. provisional application 62/619,802, filed on Jan. 20, 2019 and U.S. provisional application 62/631,948, filed on Feb. 18, 2019. The entire disclosure both of the previous applications 62/619,802 and 62/631,948 are included herein at least by reference.

BACKGROUND OF THE INVENTION

1. Field of the Invention

The present invention is in the technical area of Fintech, General Purpose Reloadable Card Aggregation and aggregation software.

2. Discussion of the State of the Art

As the $21^{st}$ century proceeds we see more and more credit, debt, gift and loyalty cards being used ubiquitously throughout the world. The typical user has a plurality of cards at their disposal. The problem is that with so many cards on hand it is difficult to keep track of their use. Many users receive gift cards from friends and family. These are particularly hard to keep track of. Many of these cards only work at set locations. As gift cards age they get forgotten and or lost if not used within a reasonably short time after acquisition. Crypto currencies are also becoming more widely used to purchase goods and or services.

What is clearly needed is a platform that lets you consolidate all cards of any type as well as crypto currencies into an app (to manage all things money) on a smart device or smart phone that enables a user to fund a single semi smart Static GPR card from multiple funding sources set up in advance by a user. This single card can be used just like any other card to purchase goods or services at a POS or even on the internet in another embodiment. The internet backbone and the associated application programming interfaces needed to make this happen are now available and fast enough to switch from one funding source to another funding source in under a second.

SUMMARY OF THE INVENTION

A general purpose reloadable transaction card is taught comprising in one a magnetic stripe, an EMV chip, an NFC wireless communications, capability, BLE blue tooth antenna communications capability, a rechargeable battery, a touch screen resident on the general purpose reloadable credit card, a plurality of selection items capable of making a selection on the card. Characterized in that a user may select one of a plurality of selection items on the card or initiate a touch on a touch screen to select an indicia to initiate a financial transaction.

In another embodiment the transaction card the selection of a selection item or a touch on the touch screen selects sends a communication to an API service provider housing the all of the financial datasets preloaded by the user In one embodiment the transaction card wherein the selection of a selection item or a touch on the touch screen selects sends a communication to an API service provider housing the all of the financial datasets preloaded by the user. The transaction card of claim 1 wherein the selection of a selection item or a touch on the touch screen selects sends a communication to an API service provider housing the all of the financial datasets preloaded by the user.

In another embodiment the transaction card wherein the selection of a selection item or a touch on the touch screen selects sends a communication by bluetooth to a smartphone which then relays the communication to an API service provider housing the all of the financial datasets preloaded by the user.

In another embodiment of the invention the transaction cards selection of a selection item or a touch on the touch screen selects sends a communication by NFC to a POS which then relays the communication to an API service provider housing the all of the financial datasets preloaded by the user.

In another embodiment the selection of a selection item or a touch on the touch screen selects sends a communication by EMV chip through a network to an API service provider housing the all of the financial datasets preloaded by the user.

In one embodiment the transaction card of the claimed invention wherein the selection of a selection item or a touch on the touch screen selects and sends a communication by micro sim to the cellular network which then relays the communication to an API service provider housing the all of the financial datasets preloaded by the user.

In one embodiment the transaction card of the claimed invention the selection of a selection item or a touch on the touch screen selects a funding source of a user to initiate a financial transaction wherein a funding choice made by a user and is directed and communicated to a third party API service provider housing the financial datasets of the users preloaded credit card transaction associated data and virtual currency sufficient to complete a transaction at a physical POS or an internet virtual POS.

In another embodiment of the invention the transaction card the invention the selection of a selection item or a touch on the touch screen selects a funding source of a user to initiate a financial transaction wherein a funding choice made by a user is communicated to a third party API service provider housing datasets of a plurality of the users preloaded personal credit card transaction card data and virtual currency data and wherein the users selection may be any of the preloaded transaction datasets or virtual currency. The transaction of the invention wherein the funding source for general purpose reloadable credit card is chosen by a user on the general purpose reloadable credit card and communicated to a smart application resident on a smart phone from the general purpose reloadable credit card and further communicated to a third party API service provider.

The third party API service provider of the invention wherein funding sources are credit card accounts for a single user. The third party API service provider of the invention wherein funding sources are gift or loyalty card accounts for a single user. The third party API service provider of the invention wherein funding sources may be a virtual currency account and further the third party API service provider of the invention may have the ability to convert and calculate the real-time fiat value of said virtual currency enabling the transaction card to make a purchase wherever Visa and MasterCard are accepted The transaction card of the invention wherein a connection may be made to the API service provider so that a funding source may be chosen by the user on the physical card by a user for a transaction through an EMV chip and further through the POS rails network (the normal way), an NFC chip through the POS network to the API service provider, through a magnetic stripe through the POS network to the API service provider, through the cards BLE capability to communicate the smartphone to the cellular network to the internet to the API service provider, magnetic stripe through the POS network to the API service provider, through the cards MicroSim capability to communicate the smartphone to the cellular network to the internet to the API service provider.

The general purpose reloadable transaction card comprising at least a magnetic stripe;

an EMV chip;

NFC wireless communications capability;

BLE blue tooth antenna communications capability;

a rechargeable battery;

a touch screen resident on the general purpose reloadable credit card;

a plurality of selection items capable making a selection characterized in that a user may select one of a plurality of selection items on the card or initiate a touch on a touch screen to select an indicia to initiate a financial transaction and further that the initiation of a transaction may be accomplished by the users or another authorized voice.

DETAILED DESCRIPTION

Figure 1:
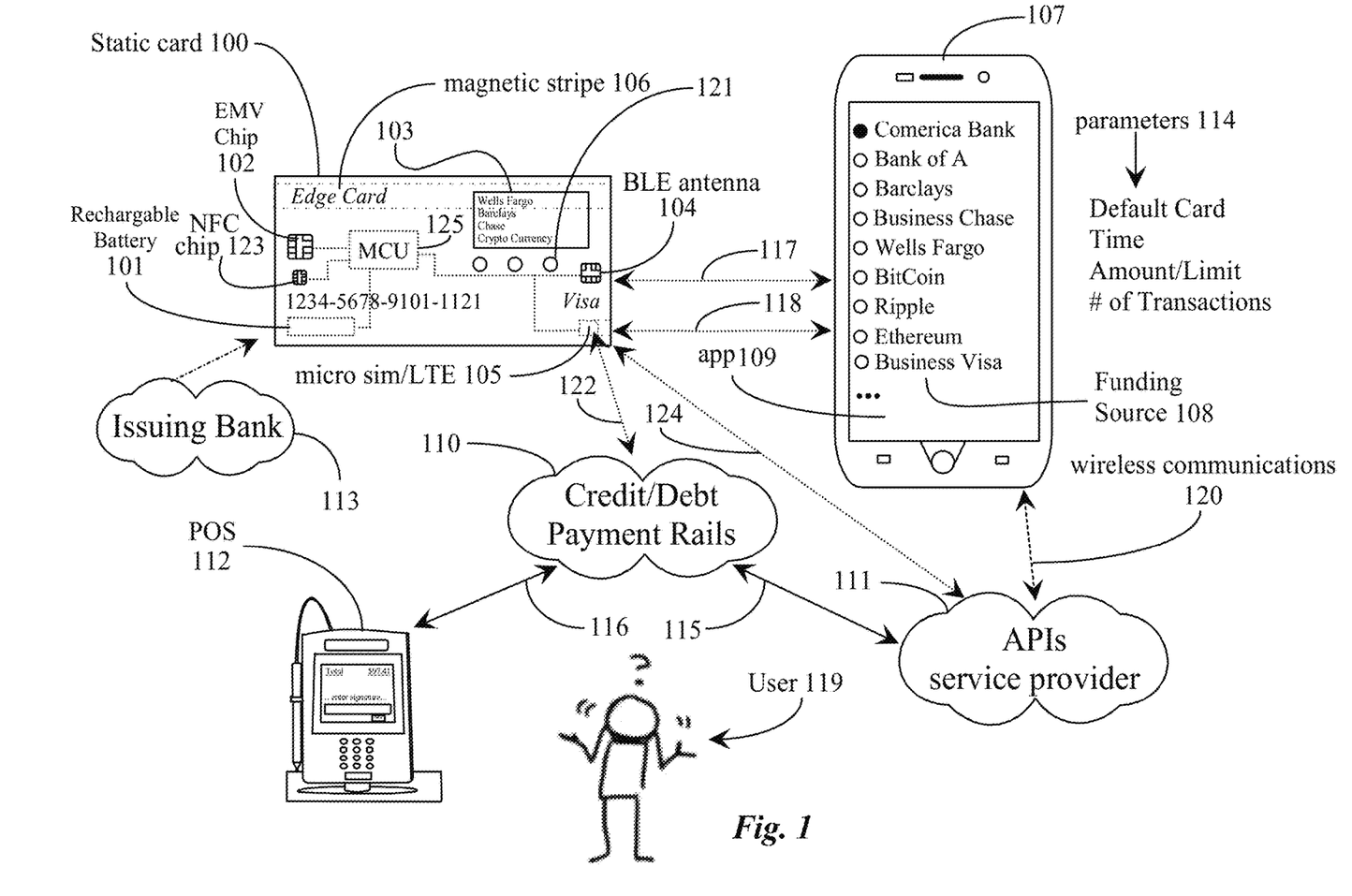
FIG. 1 is an illustration of a platform that enables a user to manage debit and Credit cards according to one embodiment of the invention.

FIG. 1 utilizes the elements below which together enable a system in which a user can manage funding sources for a smart GPR card in one of the most secure ways possible. Figure one contains the following elements:

100 Static General Purpose Re-loadable card issued by bank 113, 101 Re-chargeable Battery for operating BLE capability, micro SIM card and other elements of card 100, 102 EMV chip—secure element within, 103 Color touch enabled screen, 104 Blue tooth low energy antenna, 105 LTE enabled nano or MicroSim card capable of connecting to the cellular network and the backbone of the internet, 106 Magnetic stripe capable of initiating this type of transaction, 107 Smart device or smart phone. The IOT device can be a watch, ring, smart phone or any other IOT device with the components needed to complete transactions in the modality on the invention. The invention contains 108 Choice of funding source within app, 109 Smart digital wallet application, 110 Credit-Debt payment rails, 111 Third party platform supplying or providing application programming interfaces APIs, 112 Point of service device with the optional capability of monitoring cryptocurrency value and exchanging that value to fiat so that a credit card of any type can be used on the fly to spend crypto currency on the fly just like a credit card. 115 Communications channel between third party platform supplying APIs and Credit-Debt payment rails enabling through an app to set 114 Pre-set parameters, 116 communications between Point of service device and Credit/Debit Payment rails, 117 Wireless Blue tooth communication between smart device/smartphone 107, 118 Wireless communications between smart device/smartphone 107 and LTE enabled nano or MicroSim card, a user 119. 120 Communications between the third party API provider and smart app 109 and smart phone 107, 121 Buttons for selecting a funding source resident on GPR card 100 including a virtual currency. 122 Is an LTE enabled nano SIM card/chip which enables communications over the wireless Cellular networks and the internet backbone. 123 Is an NFC chip enabling near field communications between GPR card 100 and an NFC enabled POS terminal, smartphone of other capable IOT devices. 124 is a communications channel/link to the cellular network, API cloud (there could be more than one APIs involved) so connection 124 can connect to smart phone 107, card 100, rails 110, POS 112 and issuing bank. 125 Is an MCU which is a micro controller unit or a MPU microprocessor unit either of which may control the functions of card 100 as can be seen by dotted lines extending from MCU or MPU to the other various elements of card 100.

FIG. 1 is an illustration of one embodiment of the present invention which enables a consumer to manage funding sources for a Static General Purpose Re-loadable (here after GPR Card 100). In this embodiment a static card with three payment technologies is provided. During manufacture GPR card 100 is provisioned with payment technologies including but not limited to magnetic stripe technology, EMV chip technology and NFC technology. Re-chargeable Battery 101 may be charged by a nano solar panel embedded in the cards surface. The re-chargeable battery may also be charged with a mini charging port. Battery 101 may also be charged through inductive charging. In one embodiment any charging technology that exists in the public domain may be used to recharge battery 101. MCU 125 is provided to manage all of the other elements of card 100 such as BLE antenna and communications, LTE micro sim card 105, touch screen 103, NFC capability 123, EMV chip 102 and buttons 121 as well as Sim card 105.

Figure 3:
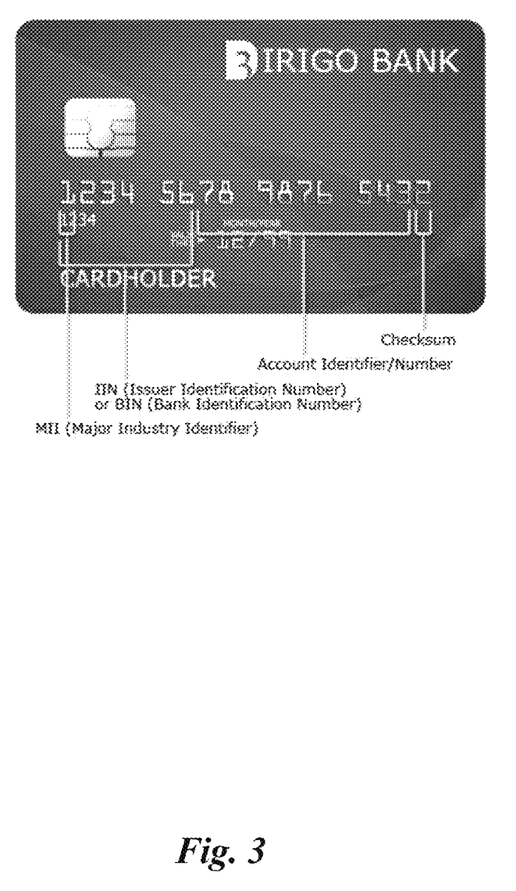
FIG. 3 is an illustration of a card number on a credit card and meaning of various parts of the card number.

GPR card 100 is also provisioned with a 16 digit card number from issuing bank 113. As we can see in FIG. 3 the 16 digit number identifies the issuer through an issuer identification number and has an account identifier as well. In one embodiment the Bin or Issuer ID number and or account identifier directs any POS terminal or internet virtual terminal to look for a funding source for GPR card 100 at a third party API service provider during any POS, virtual terminal or virtual POS transaction. Funding source 108 may be changed at any time by user 119.

In one embodiment, during manufacture, this smart GPR card is provisioned with a color screen 103, a BLE Blue tooth light wireless technology antenna 104, an NFC chip 123, and a MicroSim/LTE card/chip 105. GPR card 100, enabled with these technologies, may communicate with smart financial mobile application 109 residing on device or smart phone 107 through wireless technologies communications links 117 and or 118. Wireless link 117 is a direct wireless BLE communications link to smart app residing on smart phone 107. The wireless connection here may be any known wireless technology. LTE stands for Long-Term Evolution (LTE) which is a standard for high-speed wireless communication for mobile devices and data terminals, based on the GSM/EDGE and UMTS/HSPA technologies. It increases the capacity and speed using a different radio interface together with core network improvements. LTE is the upgrade path for carriers with both GSM/UMTS networks and CDMA2000 networks. The Nano SIM is both smaller and approximately 15% thinner than the earlier Micro SIM (3FF) standard as well as the Mini SIM (2FF) cards that were ubiquitous for many years and people commonly refer to simply as SIM cards. Communications link 118 is an LTE nano SIM card enabling the card 100 to communicate with the internet via a cellular network, payment rails 110 and the smart app 109 residing on smart phone 107 either directly or through the internet, proxy server or cloud.

GPR card is issued from a bank 113. Third party API service provider 111 may, in one embodiment, broker the deal for the purchase of the card numbers. GPR card 100 may be personalized with the purchasers or user's name if user is willing to wait for mail delivery. GPR card 100 may also be sold retail. The user's name may be displayed on screen 103. Screen 103 may also display the logo of the funding source while a transaction is in progress. The screen may also turn bright green displaying APPROVED when a transaction is approved. The indicia on the screen may display any desired logo, name of other indicia.

Card 100 may be swiped to initiate a transaction via its magnetic stripe 106; Card 100 may be inserted into a Point of service (hereafter POS) device utilizing the EMV chip 102 to initiate a transaction; Card 100 may also taped or may be waved near a Near Field Communications (hereafter NFC) enabled POS device to initiate a transaction. GPR card 100 may use any of the three technologies to initiate a transaction. In another embodiment GPR card 100 may be used on the internet at a virtual POS or virtual terminal to initiate a transaction. This will be discussed in further detail later in this specification. In this embodiment a smart device or a smart phone 107 is provided. Loaded or installed on this smart device or smart phone 107 is a smart digital wallet application 109. Smart app 109 has much functionality including displaying funding sources for GPR card 100.

A third party API service provider 111 is also provided in this preferred embodiment. API service provider 111 provides Application Programming Interfaces (hereafter APIs). An application programming interface (API) is a set of subroutine definitions, protocols, and tools for building application software. In general terms, it is a set of clearly defined methods of communication between various software components. An API may be for a web-based system, operating system, database system, and computer hardware or software library. For our purposes the APIs enable seamless communication between various elements of the invention may include but may not limited to issuing bank 113, Payment rails 110, API entity 111, smart phone 107, smart app 109, Card 100 and POS 112.

Third party API platform service provider 111 also lets a user or business program and customize the card experience for example user 119 may program funding sources for GPR card 100. This is just one example of funding customization. Funding for card 100 may be a plurality of sources including bank accounts, checking accounts, credit card accounts and even crypto currencies. User 119 has the flexibility, through third party API platform service provider 111, to customize the funding sources for card 100 on the fly. For example the funding source for GPR card 100 may be selected seconds before processing a transaction at a POS terminal whether it is physical or virtual.

In one preferred embodiment. User 119 owns a business and therefore has cards from his business as well. He also has cards from Visa, MasterCard, American express and Discover. User 119 is very popular with his business associates, personal acquaintances, family and friends. He receives many gifts in the form of Gift cards etc. . . . .

User 119 has 12 credit, debit, gift and loyalty cards. User has a hard time managing all of these cards and he desperately desires a way simplify his card life.

User 119 has also been dabbling in crypto currencies. User 119 bought Bitcoin, Ripple and Ethereum when they just started. User has held onto his crypto currencies until now. His cryptocurrency value has gone from a $500.00 initial investment to well over a 500,000.00. User 119 wants to manage and utilize his crypto currencies as well as his credit, debit, gift and loyalty cards to buy goods and services.

User 119 buys a smart GPR card 100 enabling him to consolidate all of the various cards he owns. User will first activate his GPR card 100 using his 16 digit card number either through the application 109, a web site, by phone or via any other known activation technologies. In a preferred embodiment card 100 is activated through app 109. Once activated GPR card 100 is ready for use.

In one embodiment user 119 has set up smart digital wallet app 109 (hereafter smart app 109) on his smart phone. Application 109 enables user 119 to add all of his cards and his crypto currencies (funding sources for GPR card 100) into app 109. The user may add his cards by taking a picture of them for the major cards like Visa MasterCard, Discover and America Express. If any of the cards are enabled with a bar code this bar code may be read with camera of the smart device or smart phone 107 or a specialized bar code reader adapted to smart phone 107 for the reading of the bar codes. User 119 may also add his cards on the web through the site of the third party API service provider. User may also add his cards manually by entering the 16 digit card number directly into the smart financial app 109. If necessary the user 119 may swipe cards with a portable card reader or scanner to add them to his app 109. Portable card reader may in one embodiment be a bluetooth card reader. All cards entered must be activated either before entry or user may activate cards through app 109. User 119 may add his crypto currencies as a funding source for GPR card 100 through the third party API service provider as well.

Once the user has added all of his cards and crypto currency accounts into app 109 app the user may begin to set default cards for funding his GPR card 100 for use based on different criteria. Once the card defaults are set the user may begin to use GPR card 100 at his convenience (after activation). Activation is a straight forward process of entering the 16 digit card number into smart app 109 and following the prompts.

Let's walk through a transaction with our user 119. User 119 enters Best Buy with the intention of buying some wireless ear buds (black!). The user decides that he would like to use his Comerica Visa card tied to his bank account. His visa has already been pre-loaded into app 109 and set as default funding source for his GPR card 100. He finds the ear buds and proceeds to check out. The user 119 swipes GPR card 100 at POS 112. The POS communicates over payment network rails 110 via link 116 and 115 looking for a funding source. Based on information in the GPR cards' 16 digit number the payment rails 110 are directed to look for a funding source at third party API service provider 111. Payment network rails 110 find the funding source set by user 119 which is the users Comerica Visa card account. Once the funding source is found the amount of the ear bud transaction is deducted from the funding source Comerica Visa card account and added to the GPR card account. Once the GPR card 100 is funded from the Comerica Visa card account the payment rails charge the transaction amount to the GPR card 100s account at which point the transaction is complete and the balance on the GPR card's 100 account is zero. In fact there is never a balance left on the account associated with GPR card account. This aspect of the invention increases security tremendously. This transaction can be completed in as little time as 200 milliseconds.

In another embodiment user 119 wants to buy something for his business and therefore needs to change the funding source for GPR card 100. Since he has not previously set his Chase business card as default he can choose his Chase business card to fund GPR card 100 via screen 103 manufactured into GPR card 100. He can swipe up and down or left to right (depending on setup) until his Chase business card comes into view and then select or tap it or he can use buttons 121. The left button scrolls up and the right button scrolls down. The center button is the select button. These buttons and touch screen may be set up to the users liking and may be different from card to card. The user scrolls and finds his Chase business card and selects it with the center button or taps it on the screen. Once user 100 selects his Chase business card for a funding source, card 100 transmits the selection via BLE capability 104 to smart phone or device 107 over wireless communication channel 117 and the smart app 109 residing on smartphone 107 receives this choice and transmits this funding choice to third party API service provider 111 via cellular network capability on smart phone 107. Funding choice may also be transmitted via the internet if the smart phone is connected to WiFi or a hot spot. In one embodiment the funding choice may be transmitted via cellular network via micro SIM LTE chip 105 resident on GPR card 100. The choice of funding sources may also be initiated through an SMS, a phone call, selection on smart app 109, through a web site or other known commutations methods.

Now that the funding source has been changed user can now checkout at POS. The process from this point forward for this transaction is the same as for the first example. The POS communicates over payment network rails 110 looking for a funding source. Based on information in the GPR card's 16 digit number the payment rails 110 are directed to look at third party API service provider 111. Payment network rails 110 find the funding source which is now the user's Business card. Once this funding source is found the amount of the business transaction is deducted from the funding source and added to the GPR card account and charged to the GPR card account in about 200 milliseconds.

User 119 may set a default card for business and one for personal expenses. The user may also set default cards by amount and credit limit. For instance if a charge is over a certain amount the application 109 will default to a different card based on the available credit. The user may set a timer period for a certain funding choices. Say the user is doing all of his Christmas shopping and wants to use a certain card, Visa, for instance, for a set period of time which may be minutes, hours or days. The user may shop during that time period and his pre-selected Visa card will be the default funding source for that time period. User 119 may also set a limit on the number of transactions for a card chosen as a funding source in app 109. The user may also change his choice of funding cards based on his location. If the user is in or near the Costco parking lot or in the store the smart financial app 109 will change the default funding source card to his Costco card.

Furthermore his smart app may make funding choices based on his location and direction of travel and further his location, direction of travel and speed of travel. The smart financial app will learn the user's behavior based on his history so if he uses his Master Card only as a funding source when he is at home (location) the app will default to that historical funding source when the user is at home unless a different funding choice is made overriding his historical funding choice behavior. If, based on his recorded history, he uses only one card while traveling the smart app will know when he is traveling based on his location, direction and speed of travel. The funding source may be changed accordingly. The smart app will also have intelligence from merchants that user 119 generally uses, such as which card does user select as a funding source at this particular merchant? If he uses a certain card as a funding source the majority of the time at this merchant site then the app 109 will change funding source accordingly. User 119 may override any preset funding source at will.

If user 119 is in Las Vegas and he has been to Vegas before and he has a particular funding choice behavior in Vegas smart app 109 will change his funding sources accordingly. The user can set the app to suggest funding choices based on behavior and history or change them based on behavior and history. User can also go to the map function in smart app 109 and point at any place on earth. Once the place is selected the funding choices for those places will be displayed. If user 119 is going on a trip he can preselect funding choices based on location in advance.

In another embodiment user 119 wishes to use his crypto currency "Ripple" to make a purchase. In this embodiment user 119 selects items to purchase and proceeds to a POS for checkout. He takes out his smart phone 107 and opens smart financial app 109. He scrolls to select his crypto currency Ripple as a funding source 108. He selects Ripple as a funding source. App 109 communicates through Internet or cellular link 120 to third party API service provider 111. Ripple is set as default for at least this transaction. He proceeds to POS and uses any of the 3 technologies discussed earlier EMV, NFC or magnetic stripe. Once he initiates a transaction through the payment rails 110 the payment rails 110 knows to seek a funding source through link 116 and 115 based on static GPR card 100 card details (16 digit number) at third party API service provider 111. Funding source is found through the rails and communications link 115 at API service provider 111. API service provider 111 has APIs that check crypto currency value for Ripple and deduct the value from user's crypto currency Ripple account (including any prearranged fees) and funds the account associated with GPR card 100. The funds are then immediately deducted from account associated with GPR card 100 completing the transaction.

FIG. 1 is an illustration of one preferred embodiment of the present invention which enables a consumer to manage funding sources for a Static General Purpose Re-loadable (here after GPR Card 100). In this embodiment a static card with three payment technologies is provided. During manufacture GPR card 100 is provisioned with payment technologies including but not limited to magnetic stripe technology, EMV chip technology and NFC technology. Re-chargeable Battery 101 may be charged by a nano solar panel embedded in the cards surface. The re-chargeable battery may also be charged with a mini charging port. Battery 101 may also be charged through inductive charging. In one embodiment any charging technology that exists in the public domain may be used to recharge battery 101. MCU 125 is provided to manage all of the other elements of card 100 such as BLE antenna and communications, LTE micro sim card 105, touch screen 103 NFC capability 123, EMV chip 102 and buttons 121.

GPR card 100 is also provisioned with a 16 digit card number. As we can see in FIG. 3 the 16 digit number identifies the issuer through an issuer identification number and has an account identifier as well. In one embodiment the Bin or Issuer ID number and or account identifier directs any POS terminal or internet virtual terminal to look for a funding source for GPR card 100 at a third party API service provider during any POS, virtual terminal or virtual POS transaction. Funding source 108 may be changed at any time by user 119.

In one embodiment, during manufacture, this smart GPR card is provisioned with a color screen 103, a BLE Blue tooth light wireless technology antenna 104, an NFC chip 123, and a MicroSim/LTE card/chip 105. GPR card 100, enabled with these technologies, may communicate with smart financial mobile application 109 residing on device or smart phone 107 through wireless technologies communications links 117 and or 118. Wireless link 117 is a direct wireless BLE communications link to smart app residing on smart phone 107. The wireless connection here may be any known wireless technology.

LTE stands for Long-Term Evolution (LTE) which is a standard for high-speed wireless communication for mobile devices and data terminals, based on the GSM/EDGE and UMTS/HSPA technologies. It increases the capacity and speed using a different radio interface together with core network improvements. LTE is the upgrade path for carriers with both GSM/UMTS networks and CDMA2000 networks. The Nano SIM is both smaller and approximately 15% thinner than the earlier Micro SIM (3FF) standard as well as the Mini SIM (2FF) cards that were ubiquitous for many years and people commonly refer to simply as SIM cards. Communications link 118 is an LTE nano SIM card enabling the card 100 to communicate with the internet via a cellular network, payment rails 110 and the smart app 109 residing on smart phone 107 either directly or through the internet, proxy server or cloud.

GPR card is issued from a bank 113. Third party API service provider 111 may, in one embodiment, broker the deal for the purchase of the card numbers. GPR card 100 may be personalized with the purchasers or user's name if user is willing to wait for mail delivery. GPR card 100 may also be sold retail. The user's name may be displayed on screen 103. Screen 103 may also display the logo of the funding source while a transaction is in progress. The screen may also turn bright green displaying APPROVED when a transaction is approved. The indicia on the screen may display any desired logo, name of other indicia.

Card 100 may be swiped to initiate a transaction via its magnetic stripe 106; Card 100 may be inserted into a Point of service (hereafter POS) device utilizing the EMV chip 102 to initiate a transaction; Card 100 may also taped or may be waved near a Near Field Communications (hereafter NFC) enabled POS device to initiate a transaction. GPR card 100 may use any of the three technologies to initiate a transaction. In another embodiment GPR card 100 may be used on the internet at a virtual POS or virtual terminal to initiate a transaction. This will be discussed in further detail later in this specification.

In this embodiment a smart device or a smart phone 107 is provided. Loaded or installed on this smart device or smart phone 107 is a smart digital wallet application 109. Smart app 109 has much functionality including displaying funding sources for GPR card 100.

A third party API service provider 111 is also provided in this preferred embodiment. API service provider 111 provides Application Programming Interfaces (hereafter APIs). An application programming interface (API) is a set of subroutine definitions, protocols, and tools for building application software. In general terms, it is a set of clearly defined methods of communication between various software components. An API may be for a web-based system, operating system, database system, and computer hardware or software library. For our purposes the APIs enable seamless communication between various elements of the invention may include but may not limited to issuing bank 113, Payment rails 110, API entity 111, smart phone 107, smart app 109, Card 100 and POS 112.

Third party API platform service provider 111 also lets a user or business program and customize the card experience for example user 119 may program funding sources for GPR card 100. This is just one example of funding customization. Funding for card 100 may be a plurality of sources including bank accounts, checking accounts, credit card accounts and even crypto currencies. User 119 has the flexibility, through third party API platform service provider 111, to customize the funding sources for card 100 on the fly. For example the funding source for GPR card 100 may be selected seconds before processing a transaction at a POS terminal whether it is physical or virtual.

In one preferred embodiment. User 119 owns a business and therefore has cards from his business as well. He also has cards from Visa, MasterCard, American express and Discover. User 119 is very popular with his business associates, personal acquaintances, family and friends. He receives many gifts in the form of Gift cards etc. . . . . .

User 119 has 12 credit, debit, gift and loyalty cards. User has a hard time managing all of these cards and he desperately desires a way simplify his card life. User 119 has also been dabbling in crypto currencies. User 119 bought Bitcoin, Ripple and Ethereum when they just started. User has held onto his crypto currencies until now. His cryptocurrency value has gone from a $500.00 initial investment to well over a 500,000.00. User 119 wants to manage and utilize his crypto currencies as well as his credit, debit, gift and loyalty cards to buy goods and services.

User 119 buys a smart GPR card 100 enabling him to consolidate all of the various cards he owns. User will first activate his GPR card 100 using his 16 digit card number either through the application 109, a web site, by phone or via any other known activation technologies. In a preferred embodiment card 100 is activated through app 109. Once activated GPR card 100 is ready for use.

In one embodiment user 119 has set up smart digital wallet app 109 (hereafter smart app 109) on his smart phone. Application 109 enables user 119 to add all of his cards and his crypto currencies (funding sources for GPR card 100) into app 109. The user may add his cards by taking a picture of them for the major cards like Visa MasterCard, Discover and America Express. If any of the cards are enabled with a bar code this bar code may be read with camera of the smart device or smart phone 107 or a specialized bar code reader adapted to smart phone 107 for the reading of the bar codes. User 119 may also add his cards on the web through the site of the third party API service provider. User may also add his cards manually by entering the 16 digit card number directly into the smart financial app 109. If necessary the user 119 may swipe cards with a portable card reader or scanner to add them to his app 109. Portable card reader may in one embodiment be a bluetooth card reader. All cards entered must be activated either before entry or user may activate cards through app 109. User 119 may add his crypto currencies as a funding source for GPR card 100 through the third party API service provider as well.

Once the user has added all of his cards and crypto currency accounts into app 109 app the user may begin to set default cards for funding his GPR card 100 for use based on different criteria. Once the card defaults are set the user may begin to use GPR card 100 at his convenience (after activation). Activation is a straight forward process of entering the 16 digit card number into smart app 109 and following the prompts. Let's walk through a transaction with our user 119. User 119 enters Best Buy with the intention of buying some wireless ear buds (black!). The user decides that he would like to use his Comerica Visa card tied to his bank account. His visa has already been pre-loaded into app 109 and set as default funding source for his GPR card 100. He finds the ear buds and proceeds to check out. The user 119 swipes GPR card 100 at POS 112. The POS communicates over payment network rails 110 via link 116 and 115 looking for a funding source. Based on information in the GPR cards' 16 digit number the payment rails 110 are directed to look for a funding source at third party API service provider 111. Payment network rails 110 find the funding source set by user 119 which is the users Comerica Visa card account. Once the funding source is found the amount of the ear bud transaction is deducted from the funding source Comerica Visa card account and added to the GPR card account. Once the GPR card 100 is funded from the Comerica Visa card account the payment rails charge the transaction amount to the GPR card 100 account at which point the transaction is complete and the balance on the GPR card's 100 account is zero. In fact there is never a balance left on the account associated with GPR card account. This aspect of the invention increases security tremendously. This transaction can be completed in as little time as 200 milliseconds.

In another embodiment user 119 wants to buy something for his business and therefore needs to change the funding source for GPR card 100. Since he has not previously set his Chase business card as default he can choose his Chase business card to fund GPR card 100 via screen 103 manufactured into GPR card 100. He can swipe up and down or left to right (depending on setup) until his Chase business card comes into view and then select or tap it or he can use buttons 121. The left button scrolls up and the right button scrolls down. The center button is the select button. These buttons and touch screen may be set up to the users liking and may be different from card to card. The user scrolls and finds his Chase business card and selects it with the center button or taps it on the screen. Once user 100 selects his Chase business card for a funding source, card 100 transmits the selection via BLE capability 104 to smart phone or device 107 over wireless communication channel 117 and the smart app 109 residing on smartphone 107 receives this choice and transmits this funding choice to third party API service provider 111 via cellular network capability on smart phone 107. Funding choice may also be transmitted via the internet if the smart phone is connected to WiFi or a hot spot. In one embodiment the funding choice may be transmitted via cellular network via micro SIM LTE chip 105 resident on GPR card 100. The choice of funding sources may also be initiated through an SMS, a phone call, selection on smart app 109, through a web site or other known commutations methods.

Now that the funding source has been changed user can now checkout at POS. The process from this point forward for this transaction is the same as for the first example. The POS communicates over payment network rails 110 looking for a funding source. Based on information in the GPR card's 16 digit number the payment rails 110 are directed to look at third party API service provider 111. Payment network rails 110 find the funding source which is now the user's Business card. Once this funding source is found the amount of the business transaction is deducted from the funding source and added to the GPR card account and charged to the GPR card account in about 200 milliseconds.

User 119 may set a default card for business and one for personal expenses. The user may also set default cards by amount and credit limit. For instance if a charge is over a certain amount the application 109 will default to a different card based on the available credit. The user may set a period of time for a certain funding choices. Say the user is doing all of his Christmas shopping and wants to use a certain card, Visa, for instance, for a set period of time which may be minutes, hours or days. The user may shop during that time period and his pre-selected Visa card will be the default funding source for that time period.

User 119 may also set a limit on the number of transactions for a card chosen as a funding source in app 109. The user may also change his choice of funding cards based on his location. If the user is in or near the Costco parking lot or in the store the smart financial app 109 will change the default funding source card to his Costco card. Furthermore his smart app may make funding choices based on his location and direction of travel and further his location, direction of travel and speed of travel. The smart financial app will learn the user's behavior based on his history so if he uses his Master Card only as a funding source when he is at home (location) the app will default to that historical funding source when the user is at home unless a different funding choice is made overriding his historical funding choice behavior. If, based on his recorded history, he uses only one card while traveling the smart app will know when he is traveling based on his location, direction and speed of travel. The funding source may be changed accordingly. The smart app will also have intelligence from merchants that user 119 generally uses, such as which card does user select as a funding source at this particular merchant? If he uses a certain card as a funding source the majority of the time at this merchant site then the app 109 will change funding source accordingly. User 119 may override any preset funding source at will.

If user 119 is in Las Vegas and he has been to Vegas before and he has a particular funding choice behavior in Vegas smart app 109 will change his funding sources accordingly. The user can set the app to suggest funding choices based on behavior and history or change them based on behavior and history. User can also go to the map function in smart app 109 and point at any place on earth. Once the place is selected the funding choices for those places will be displayed. If user 119 is going on a trip he can preselect funding choices based on location in advance.

In another embodiment user 119 wishes to use his crypto currency "Ripple" to make a purchase. In this embodiment user 119 selects items to purchase and proceeds to a POS for checkout. He takes out his smart phone 107 and opens smart financial app 109. He scrolls to select his crypto currency Ripple as a funding source 108. He selects Ripple as a funding source. App 109 communicates through Internet or cellular link 120 to third party API service provider 111. Ripple is set as default for at least this transaction. He proceeds to POS and uses any of the 3 technologies discussed earlier EMV, NFS or magnetic stripe. Once he initiates a transaction through the payment rails 110 the payment rails 110 knows to seek a funding source through link 116 and 115 based on static GPR card 100 card details (16 digit number) at third party API service provider 111.

Funding source is found through the rails and communications link 115 at API service provider 111. API service provider 111 has APIs that check crypto currency value for Ripple and deduct the value from user's crypto currency Ripple account and funds the account associated with GPR card 100. The funds are then immediately deducted from account associated with GPR card 100 completing the transaction.

Figure 2:
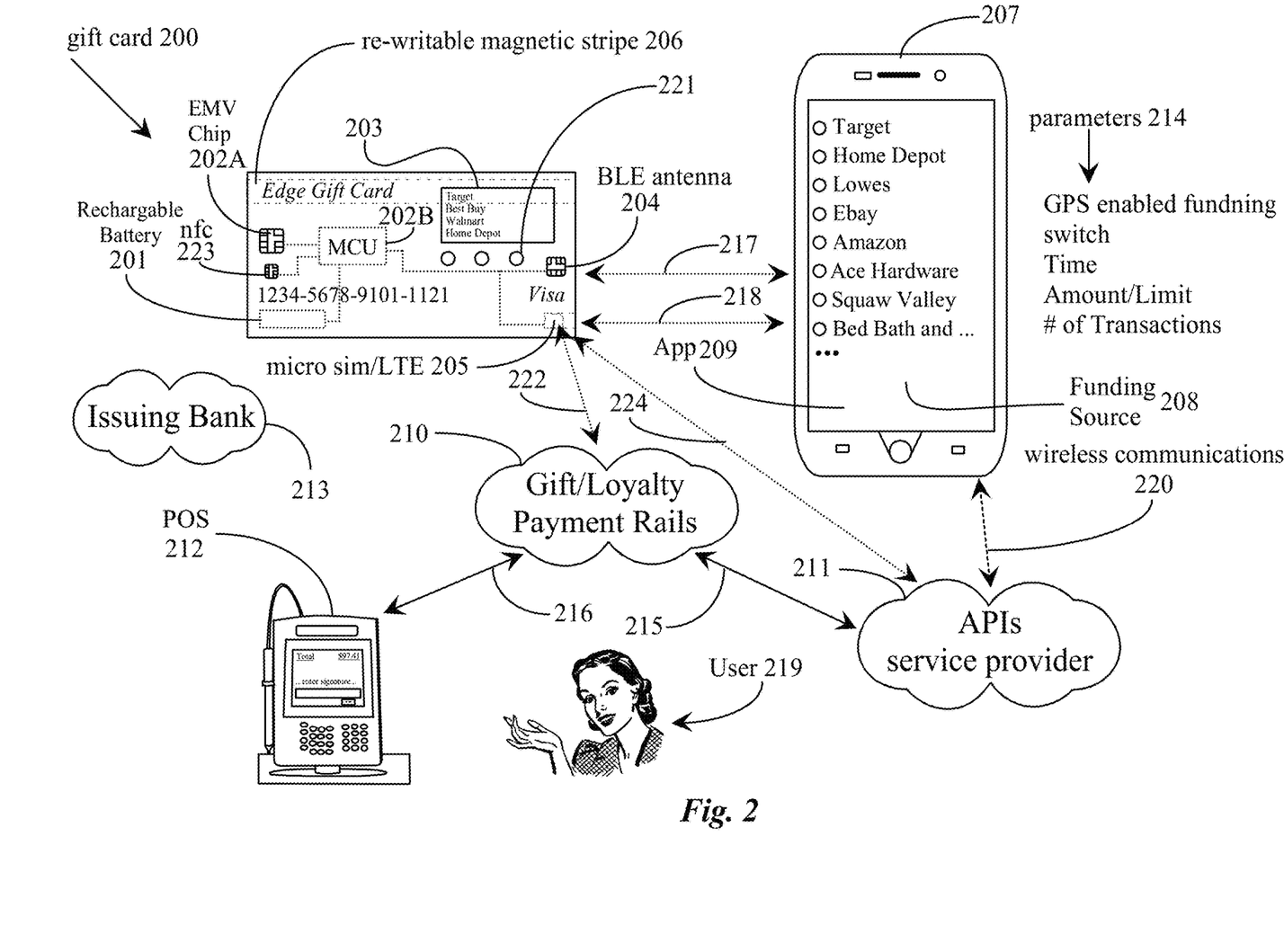
FIG. 2 is an illustration of a platform that enables a user to manage gift and loyalty cards according to one embodiment of the invention.

FIG. 2 utilizes the elements below which together enable a system in which a user can manage funding sources for a smart GPR card in one of the most secure ways possible. FIG. 2 contains the element numbers recited below:

200 is a general purpose reloadable smartcard 200, 201 is a rechargeable battery 202A is an EMV chip, 203A is an MCU which is a micro controller unit or a MPU microprocessor unit either of which may control the functions of card 100 as can be seen by dotted lines extending from MCU or MPU to the other various elements of card 200, 203 is a touch sensitive screen, 204 is a BLE antenna (Blue tooth low power) any other wireless protocol may also be utilized, 205 Is an LTE enabled nano SIM card/chip which enables communications over the wireless Cellular networks, 206 is a magnetic stripe and may be re-writable in some embodiments, 207 is a smartphone or device capable of operating mobile application 209, 210 is a payment network for gift and loyalty cards, 211 is a third party API service provider, 212 is a point of sale device, 213 is the card issuing bank, 214 is are parameters that can be set in app 209 and or API service provider, 215 indicates communication between Loyalty/Gift payment network and API service provider, 216 indicates communication between Loyalty/Gift payment network and POS 212, 217 indicates wireless communication between card 200 and phone 207, 218 is a communications link 218 is an LTE nano SIM card enabling the card 200 to communicate with the internet via a cellular network, payment rails 210 and the smart app 209 residing on smart phone 207 either directly or through the internet, 219 is user 219, 220 indicates communication between app 209 and third party API service provider 211 via Internet or cellular link 220, 221 indicated buttons for selecting a funding source on GPR card 200, 222 is an LTE nano SIM card enabling wireless communications between card 200 and payment rails 210 and the smart app 209 residing on smart phone 207 either directly or through the internet, proxy server or cloud, 223 an NFC chip and circuitry enabling NFC wireless communications between card 200 and other entities such as rails or payment network 210, 224 indicates wireless communications between card 200 and other entities such as third party API service provider 211 and other entities cover thus far in the specification.

FIG. 2 is an illustration of one preferred embodiment of the present invention which enables a consumer to manage funding sources for a Static General Purpose Re-loadable gift or loyalty card (hereafter GPR Gift Card 100). Operating along with smart application 209 residing on smart phone 207 this card operates as a gift/loyalty consolidation card.

Loyalty programs are structured marketing strategies designed by merchants to encourage customers to continue to shop at or use the services of businesses associated with each program. These programs exist covering most types of commerce, each one having varying features and rewards-scheme.

A gift card (also known as gift certificate in North America, or gift voucher or gift token in the UK) is a prepaid stored-value money card usually issued by a retailer or bank to be used as an alternative to cash for purchases within a particular store or related businesses. Gift cards are also given out by retailers and marketers as part of a promotion strategy, to entice the recipient to come in or return to the store, and at times such cards are called cash cards. Gift cards are generally redeemable only for purchases at the relevant retail premises and cannot be cashed out, and in some situations may be subject to an expiry date or fees. Visa and MasterCard credit cards produce generic gift cards which need not be redeemed at particular stores, and which are widely used for cash back marketing strategies. A feature of these cards is that they are generally anonymous and are disposed of when the stored value on a card is exhausted.

The problem with these cards is that they have become so ubiquitous for gifts and marketing that the typical sophisticated user may own a plurality of these cards. So many if fact that it is not practical to carry so many cards around on ones person.

In this embodiment GPR Gift Card 200 is also enabled with three payment technologies. During manufacture/provisioning by bank 113, GPR card 200 is provisioned with payment technologies including but not limited to magnetic stripe technology, EMV chip for Ripple and deduct the value from user's crypto currency Ripple account and funds the account associated with GPR card 100. The funds are then immediately deducted from account associated with GPR card 100 completing the transaction.

FIG. 2 is an illustration of one preferred embodiment of the present invention which enables a consumer to manage funding sources for a Static General Purpose Re-loadable gift or loyalty card (hereafter GPR Gift Card 100). Operating along with smart application 209 residing on smart phone 207 this card operates as a gift/loyalty consolidation card.

Loyalty programs are structured marketing strategies designed by merchants to encourage customers to continue to shop at or use the services of businesses associated with each program. These programs exist covering most types of commerce, each one having varying features and rewards-scheme.

A gift card (also known as gift certificate in North America, or gift voucher or gift token in the UK) is a prepaid stored-value money card usually issued by a retailer or bank to be used as an alternative to cash for purchases within a particular store or related businesses. Gift cards are also given out by retailers and marketers as part of a promotion strategy, to entice the recipient to come in or return to the store, and at times such cards are called cash cards. Gift cards are generally redeemable only for purchases at the relevant retail premises and cannot be cashed out, and in some situations may be subject to an expiry date or fees. Visa and MasterCard credit cards produce generic gift cards which need not be redeemed at particular stores, and which are widely used for cash back marketing strategies. A feature of these cards is that they are generally anonymous and are disposed of when the stored value on a card is exhausted.

The problem with these cards is that they have become so ubiquitous for gifts and marketing that the typical sophisticated user may own a plurality of these cards. So many if fact that it is not practical to carry so many cards around on ones person.

In this embodiment GPR Gift Card 200 is also enabled with three payment technologies. During manufacture GPR card 200 is provisioned with payment technologies including but not limited to magnetic stripe technology.

EMV chip technology and NFC chip technology. In one embodiment, during manufacture, this smart gift/loyalty card 200 is provided with a color screen 203, a BLE (Blue Tooth light) wireless antenna 204 may also be added enabling communications with smartphone 207 and application 209. An NFC chip 223 may also be enabled on GPR Gift Card 200. This GPR Gift Card 100 in one embodiment is enabled with all of the technologies that card 100 enjoys which were previously discussed earlier in the instant specification. MCU or MPU 202B is provided to manage all of the other elements of card 200 such as BLE antenna and communications, LTE micro sim card 205, touch screen 203 NFC capability 223, EMV chip 202A and buttons 221 as can be seen by the dotted lines running from elements of card 200.

User 219 buys a smart GPR gift card 200 to consolidate all of the various cards she owns. User 219 will first activate her GPR gift card 200 using her 16 digit card number either through the application 209, a web site, by phone or via any other known activation technologies. In a preferred embodiment GPR gift card 200 is activated through app 209.

Application 209 enables user 219 to add all of her cards into app 209. The user may add her Gift/Loyalty cards by taking a picture of them for the major cards like Visa MasterCard, Discover and America Express. If any of the cards are enabled with a bar code this bar code may be read with camera of the smart device or smart phone 207 or a specialized bar code reader adapted to smart phone 207 for the reading of the bar codes. User 219 may also add her cards on the web through the site of the third party API service provider 211. User may also add her gift cards manually by entering the 16 digit card number directly into the smart financial app 209. If necessary the user 219 may swipe cards with a portable card reader or scanner to add them to his app 209. Portable card reader may in one embodiment be a Bluetooth card reader. All cards entered must be activated either before entry or user may activate cards through app 209

GPR gift card 200 has been activated and our user 219 has entered all of her gift and loyalty cards into app 209 resident on smart phone 207. User 219 decides to go shopping with her new GPR gift card 200. User enters the mall at $41^{st}$ avenue in Capitola Calif. to do some shopping. As she travels through the store the GPS functions of smart phone 207 are utilized by smart app 209. This GPS function enables smart app 209 to communicate user's location to third party API service provider 211 so that her default funding source may match user 219's location. When user 219 enters Target she finds several items she intends to purchase and heads to check out. Smart app, utilizing the functionality of smart phone 207, may recognize the presence of a POS based on the wireless signals the POS is putting out or based on the location within Target. Smart app 209 is now displaying the default funding source, Target. User at this point may change the funding source and save the Target funds or use Target as a funding source for GPR gift card 200. She decides to use Target as a funding source.

User 219 proceeds to POS and uses any of the 3 technologies discussed earlier EMV, NFS or magnetic stripe. Once she initiates transaction through the payment rails 210 the payment rails 210 knows to seek a funding source through link 216 and 215 based on GPR card 200's card details (16 digit number) at third party API service provider 211. The Target funding source is found through the rails 210 and communications link 215 at API service provider 211. The funds are then immediately deducted from the Target account and added to the account associated with GPR gift card 200 Funds are then immediately deducted from the account associated with GPR gift card 200 completing the transaction.

User 219 now decides to travel to Home Depot for some lumber. Once she pulls into the parking lot GPS functionality discussed before suggest that she change her funding source for GPR Gift card 200 to The Home Depot. User can make the change to Home Depot depending on her choice. In one embodiment App 209 does not necessarily make the changes of funding sourced based on the locations but merely suggest the funding source change based on her location. User can make the change at third party API service provider by merely tapping a button or saying "change to Home Depot" (voice recognition) she purchases her lumber and heads to check out. This time she decides to override the suggested default funding source, Home Depot, and decides to use a Visa gift card instead as she wants to save her Home Depot gift card for another time. To make the change to her Visa card user 219 views the screen 203 of her GPR gift card 200. She scrolls to her Visa using the buttons or she may select Visa on the touch screen. Either way the choice is sent to app 209 residing on smart phone 207 via BLE antenna 204. This wireless communication is indicated in FIG. 2 as wireless communications link 217. The choice of Visa could also be sent via LTE enabled micro SIM card 205 through the cellular network directly to third party API provider service 211. Either by cellular or BLE through app 209 the choice of Visa as a funding source for GPR gift card 200 will instantly be communicated to third party API Provider service 211.

User 219 approaches POS and swipes her GPR gift card 200. Gift/Loyalty payment rails 210 look to third party API service provider 211 for a funding choice, find the Visa choice and deduct the transaction amount from the Visa account and deposit funds in the transaction amount to the account associated with the GPR gift card 200. Funds in the transaction amount are immediately deducted from the GPR gift card 200 and the transaction is complete leaving a zero balance.

In another embodiment a virtual GPR card 200 may be used on the internet to initiate a transaction. User 219 is tired and does not want to travel to spend some of her gift or loyalty cards. Instead she wants to use a virtual terminal on the web. She proceeds to the EBay web site for some shopping. After she has her cart full of the items she desires she heads to checkout. During checkout she enters her card number for her GPR gift card 200. Because the 16 digit number has an identifier for third party API service provider 211 she can still utilize her gift and loyalty consolidation card 200 to pay for the items from EBay. User 219 simply grabs her card selects EBay on her screen 203 either by button or screen tap. This choice is communicated either by BLE to App 209 or via micro SIM 205 or by smartphone to app 209. App 209 then sends the EBay funding choice to third party API service provider 211. In one embodiment the choice is sent directly from GPR gift card 200 to third party API service provider 211 via cellular network 224. The funding choice of EBay could also be sent via com link 222 to the rails and then to third party API service provider 211. Third party API service provider 211 receives the choice either way and changes the funding choice to the EBay gift card. The shopping cart recognizes the EBay gift card and process the transaction accordingly. Third party API service provider 211 deducts funds from the account associated with EBay and adds the funds to GPR gift card 200. The funds are then deducted from the account associated with GPR gift card 200 and the transaction is complete.

In another embodiment user 219 has low balances on some store only gift cards and has relatively higher balance on some of the cash cards like Visa and MasterCard. User has decided to use up the balance on one of her low balance store only cards. She chooses Bed Bath and Beyond gift card. She has only 50.00 left on her Bed Bath and Beyond card. User 219 has previously set parameters in her smart application 209 resident on her smart phone 207. She has set a Hierarchy in her smart app 209. She has set her Visa cash card on which she has a 10.00 balance as a $2^{nd}$ choice for funding her GPR gift card 200 if one of her store only cards falls short on a transaction. She has also set a third MasterCard cash card with a balance of 100.00 to follow the Visa cash card if her Visa runs out of funds. She has 75.00 dollars in goods from Bed Bath and Beyond. She is now checking out. Once she swipes her card at the POS the payment rails are directed to look at third party API service provider 211 for funding. The third party API service provider 211 has been directed to deduct funds from the Visa cash card if one of the store only cards runs out of funds and to follow with MasterCard if Visa cash card runs out of funds. The payment rails only see that the funds are available. The payment rails do not see the 3 accounts used to make up the transaction. The third party API service provider as already deducted 50.00 from her account associated with her Bed Bath and Beyond store only card, 10.00 from the account associated with the account associated with her Visa cash card and 15.00 from the account associated with her MasterCard cash card account. The funds are added to the account associated with her GPR gift card 200. Payment rails see that funds are available for the transaction and deduct the amount of 75.00 from user 219's account associated with GPR gift card 200. Transaction is then complete.

Figure 4:
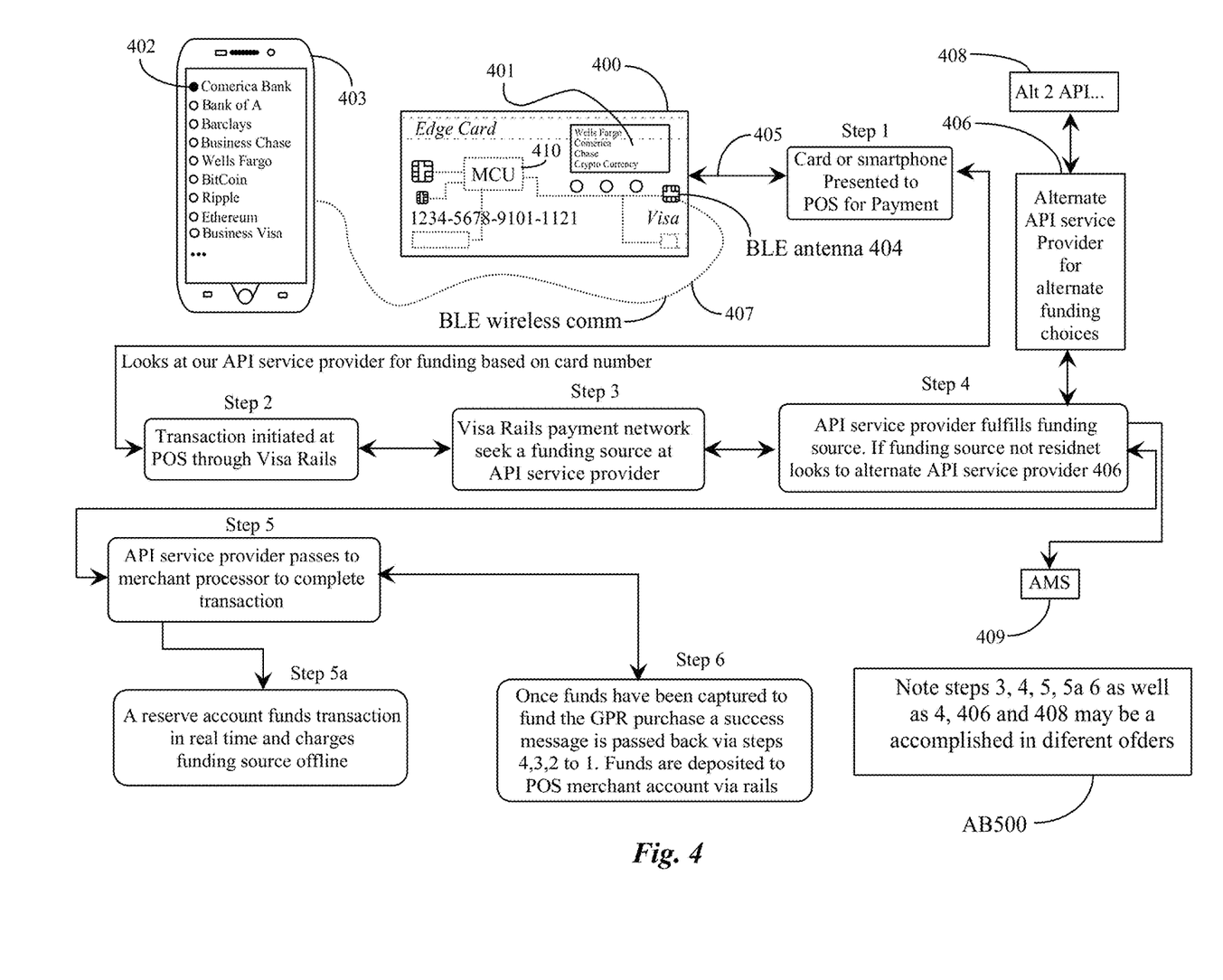
FIG. 4 is a flow diagram of a transaction according to one embodiment of the present Fig.

FIG. 4 utilizes the elements below which together enable a system in which a user can manage funding sources for a smart GPR card in one of the most secure ways possible. FIG. 4 contains the following elements:

400 is a general purpose reloadable smartcard enabling selection of funding sources for credit card or gift card transactions.

401 is a touch screen resident on smart card 400

402 is a smart mobile financial application running on a smartphone or device 403

403 is a smart phone or device capable of running smart mobile app 402

404 is a BLE capable antenna

405 indicates step one of a flow of a transaction between card and POS according to one embodiment of the present invention.

406 indicates an alternate API service provider1

408 indicates an alternate API service provider2

409 is an instance of account management software which may feed information when requested from API service providers.

FIG. 4 is an illustration of a flow chart of a transaction according to one embodiment of the present invention. Card 400 is provisioned with the same technologies as the cards in FIGS. 1 and 2. Card 400 is enabled with magnetic stripe technology, EMV chip technology and NFC technology. Card 400 is also enabled with a BLE antenna, and rechargeable battery. Card 400 also has an LTE enabled nano SIM card/chip which enables communications over the wireless Cellular networks. Card 400 is in communication via BLE channel, or any other wireless technology, with smart phone or device 403 on which smart app 402 is resident. The wireless connection between card 400 and app 402 is shown by element number 407 in FIG. 4 MCU 410 is provided to manage all of the other elements of card 400 such as BLE antenna and communications, LTE micro sim card, touch screen 401 NFC capability, EMV chip and buttons 121.

In this embodiment a funding source for a transaction is selected from card screen 401 or smart app 402 same is in previous embodiments. If funding source is selected from card 400 it is then transmitted to smart app 402 via BLE communication channel 405. Smart app 402 then transmits that funding choice to an API service provider over a cellular network as in previous embodiments. In this embodiment the API service provider in step 4 has the functionality to ensure that any funding choice is charged the amount of any transaction and deducted from that funding choice and deposited in the GPR card account resident at API service provider just before the transaction is completed. From the time the selection of a funding choice is made at the card to the time the funding choice is set at API service provider is around 200 milliseconds. In one embodiment the funding choice is made at the card and sent from card itself via LTE enabled nano SIM card/chip resident on card 400 to API service provider over cellular network.

In some embodiments there is account management software hereafter AMS 409. AMS 409 may hold (in a secure environment) and supply some of the information associated with the transaction such as account balances, default funding source selection choices and changes, credit card account limits and other information associated with funding choice, gift and or loyalty card funding choice information and other such information necessary to complete the transaction. In one embodiment API service provider, in step 4 of FIG. 4, reaches out to AMS 409 to supply some or all of this information. In other embodiments API service provider in step 4 of FIG. 4 contains all necessary information to complete the transaction.

In other embodiments the merchant processor of FIG. 4 step 5 may hold secure credit card information, account balances and other necessary secure account information for funding choice so that the transaction may be completed based in the information provided to it by API service provider at step 4 or alternate service providers 406 and 408.

In one embodiment, referring to FIG. 4 the user wants to use his Comerica card to fund his GPR card for this transaction. Once he selects Comerica on his card or makes a choice for Comerica in his smart app 402 that funding choice is transmitted to API service provider in step 4. The user, having made his funding choice, swipes inserts or otherwise initiates a transaction for a certain amount at step 1. Visa, MasterCard and American express have built a network to electronically process credit and debit card transactions. This network is sometimes referred to as payment rails or Visa Rails. For our purposes we may refer to this network using any of these terms referring to the same network. At step 2 a transaction for a certain amount is initiated through this payment network. At step 3 the network seeks a funding source for the transaction. The card number indicates where to look for a funding source. For our purposes the card number directs the network to look for a funding source at API service provider at step 4. API service provider has just been directed (from card 400 or mobile app 402) to set the funding source to Comerica bank from card 400. API service provider deducts the transaction amount from users Comerica account and funds users GPR card 400 account for the transaction amount. The payment network only sees that there are funds available.

In step 5 API service provider passes the transaction information to a merchant processor to charge the selected funding source. At step 6, once the funds have been captured or charged to fund the GPR card transaction in real-time the funds are passed back via steps 4,3,2,1 back to the point of purchase thereby funding the transaction.

In another embodiment at step 5 a reserve account or bank account contains funds to fund a series of transactions in real time once they are approved processing them later each day in batches.

In another embodiment at step 4 the API service provider will not have necessary APIs to process the transaction if the fund selection is an unusual one such as crypro currency or a credit union. If in step 4 API service provider does not have APIs for the transaction it will check an alternate API service provider for those APIs and if it finds the correct APIs it will send the transaction to step 5. Such alternate API service providers may be specialized to handle crypto currency transactions, gift card or loyalty card or credit union transactions etc. . . . . . In some embodiments the Alternate API service providers 406 and or 407 may hold other secure credit card account information that may need to be accessed by default API service provider at step 4

In another embodiment a user may wish to use a gift card if he is at a store that he has a store only gift card with enough funds to make a transaction. As long as he has loaded his gift and loyalty cards in his smart app 402 he can choose among them to fund his GPR reloadable card to make a transaction. This may, in some embodiments, require a different API service provider with different sets of APIs; however the default API service provider will have received a set of instructions from app 402 or card 400 as to which types of transactions a user is likely to make based on what he has loaded into app 402 in the first place. API service provider at step 4 has access to alternate API service provider1 (406) and API service provider2 (408) for additional types of transactions. Default API service provider will, in advance; know what type of APIs are necessary to complete any transaction a user is likely to make. If a user enters a funding source that API service provider at step 4 does not have the APIs to process and the alternate API service provider1 (406) or alternate API service provider2 (408) does not have the APIs for the type of funding source the user has attempted to enter into app 402 then the user will be notified at the time the attempt is made to load such funding sources into app 402.

In one embodiment if a user request a refund then those refunds will be directed to an ACH regular Bank account held by user in association and communication with API service providers discussed here within this specification.

In another embodiment much like step 6 in FIG. 4, If a user wants a refund than it is processed at the POS and directed to a reserve account which may hold refunds for a period of time and process refunds offline and sometimes in batches back to their original funding source.

Figure 5:
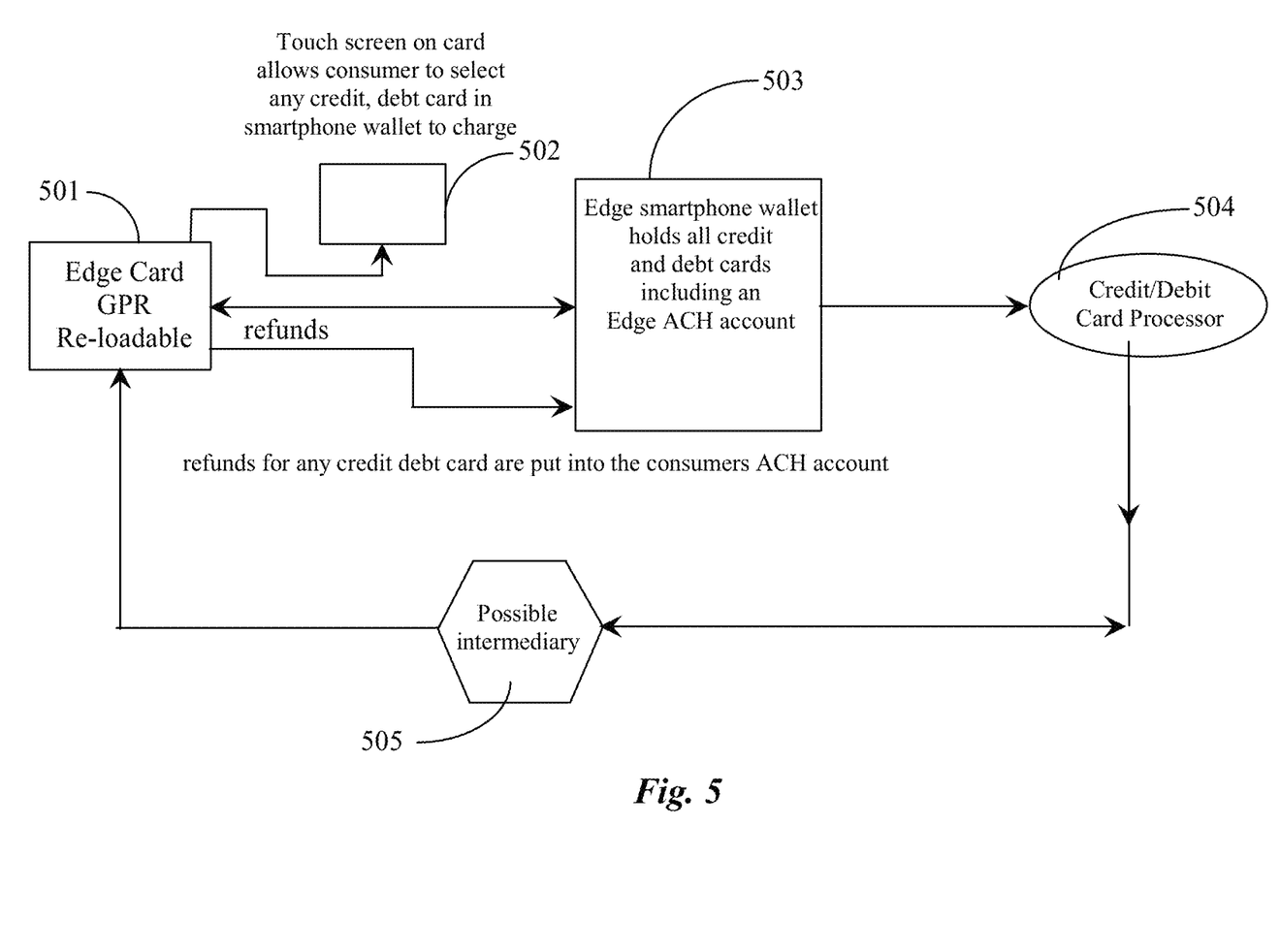
FIG. 5 is an example of a refund processed through the system of the invention.

FIG. 5 utilizes the elements below which together enable a system in which a user can manage funding or refunding services. FIG. 5 contains elements:

501 a GPR reloadable card, 502 a touch screen, 503 is a smartphone wallet has access to all credit and debit cards including an Edge ACH account to receive refunds, 504 is a debt credit card processor, 505 is a possible/proxy intermediary in the case of a user wants a refund to go to a different account.

What is claimed is:
1. A general purpose transaction card comprising:
a magnetic stripe;
an EMV chip;
an NFC wireless communications capability;
a micro SIM chip;
BLE blue tooth antenna communications capability;
a rechargeable battery;
a touch screen resident on the general purpose reloadable transaction card; and
a plurality of indicia capable of being selected on the touchscreen;
characterized in that the indicia each represent separate funding sources available through use of the card and a user may select one of the plurality of indicia on the card via functional buttons on the card or by touching the touch screen to select the indicia to initiate a financial transaction, enabling the micro SIM chip to establish direct communication, via a cellular network, between the card and an API service provider housing financial datasets associated with each funding source, wherein the card is operable to complete financial transactions with the funding sources selected by the indicia via the established direct cellular network communication.

2. The transaction card of claim 1 wherein the selection of an indicia or a touch on the touch screen selects and sends a communication via any one of the NFC and BLE to an application on a smartphone device, which relays the selection to the API service provider housing the all of the financial in an application resident on a smart phone or web interface enabling the user the freedom to select a funding source for any purchase.

3. The transaction card of claim 1 wherein the selection of the indicia selects and sends a communication by NFC to a Point Of Sale device which then relays the communication to the API service provider.

4. The transaction card of claim 1 wherein the selection of a selection indicia or a touch on the touch screen selects sends a communication by the EMV chip through a network to the API service provider.

5. The transaction card of claim 1 wherein the selection of the indicia selects a funding source which is communicated to a third party API service provider housing the financial datasets including additional associated data and virtual currency sufficient to complete a transaction at a physical POS or an internet virtual POS.

6. The transaction credit card of claim 1 wherein at least one of the indicia representing a funding source for the card is chosen by a user on the card and communicated to a smart application resident on a smart phone directly from the card and further communicated to a third party API service provider.

7. The third party API service provider of claim 6 wherein the funding sources are credit card accounts for a single user.

8. The third party API service provider of claim 6 wherein funding sources may be a virtual currency account and further the third party API service provider is enabled to convert and calculate the real-time value of said virtual currency enabling the transaction card to make a purchase wherever major credit cards are accepted.

9. The third party API service provider of claim 1 wherein funding sources are any one of a gift card, loyalty card, credit cards, and debit card accounts for a single user.

10. The transaction card of claim 1 wherein a connection may be made to the API service provider so that a funding source may be chosen by the user on the physical card by a user for a transaction through an EMV chip via any one of an NFC chip through the POS network to the API service provider, through the magnetic stripe through the POS network to the API service provider, through the cards BLE capability to communicate the smartphone to the cellular network to the internet to the API service provider, via magnetic stripe through the POS network to the API service provider, or through the micro SIM chip to communicate to the smartphone to the cellular network to the internet to the API service provider.

\* \* \* \* \*